(12) United States Patent
Michel et al.

(10) Patent No.: US 8,716,551 B2
(45) Date of Patent: May 6, 2014

(54) **PRODUCTION OF HYBRID *LACTUCA SATIVA* SEEDS**

(75) Inventors: Hervé Michel, Angers (FR); Thierry Soussin, Maze (FR)

(73) Assignee: Vilmorin, La Menitre (FR)

( * ) Notice: Subject to any disclaimer, the term of this patent is extended or adjusted under 35 U.S.C. 154(b) by 711 days.

(21) Appl. No.: 12/450,026

(22) PCT Filed: Mar. 5, 2008

(86) PCT No.: PCT/FR2008/000289
§ 371 (c)(1),
(2), (4) Date: Jan. 25, 2010

(87) PCT Pub. No.: WO2008/132310
PCT Pub. Date: Nov. 6, 2008

(65) Prior Publication Data
US 2010/0306882 A1 Dec. 2, 2010

(30) Foreign Application Priority Data
Mar. 5, 2007 (FR) .................................... 07 01589

(51) Int. Cl.
*A01H 1/00* (2006.01)
(52) U.S. Cl.
USPC .......................................... 800/271; 800/274
(58) Field of Classification Search
None
See application file for complete search history.

(56) References Cited

U.S. PATENT DOCUMENTS

| | | | |
|---|---|---|---|
| 7,102,060 B1 | 9/2006 | Knerr et al. | |
| 7,119,257 B1 * | 10/2006 | Schuitman | 800/305 |
| 7,504,562 B2 * | 3/2009 | Schut et al. | 800/305 |
| 7,569,743 B2 * | 8/2009 | Gibson et al. | 800/271 |
| 2003/0018996 A1 | 1/2003 | Avila et al. | |
| 2003/0033640 A1 | 2/2003 | Sarreal | |
| 2005/0144672 A1 | 6/2005 | Knerr et al. | |
| 2006/0021077 A1 | 1/2006 | Van Schijndel et al. | |
| 2012/0023602 A1 * | 1/2012 | Gibson et al. | 800/260 |

FOREIGN PATENT DOCUMENTS

| | | |
|---|---|---|
| JP | 2005-110623 A | 4/2005 |
| WO | WO 99/55143 A1 | 11/1999 |
| WO | WO 2007/146420 A2 | 12/2007 |

OTHER PUBLICATIONS

Goubara et al, 2003 Applied Entomology and Zoology 38(4): 571-581.*

Maisonneuve et al 1994, Theoretical and Applied Genetics 98: 96-104.*
International Search Report issued by the International Searching Authority on Nov. 26, 2008 in connection with International Application No. PCT/FR2008/000289.
Taylor et al.: "Genetic control of male fertility in *Arabidopsis thaliana*: Structural analyses of postmeiotic developmental mutants", Planta, vol. 205, No. 4, pp. 492-505 (1998).
Goubara, et. al., "Pollination effects of the sweat bee *lasioglossum villosulum* trichopse (Hymenoptera: Halictidae) on genic male-sterile lettuce," Appl. Entomol. Zool. 39 (1): 163-169 (2004).
Goubara et. al., "Flower visitors of lettuce under field and enclosure conditions," Appl. Entomol. Zool. 38 (4): 571-581 (2003).
Reznaerts et. al., "Phenotype modification by direct gene transfer: Engineered genes for fertility control and their application in hybrid seed production," Scientia Horticulturae, Elsevier Science Publishers, 55 (1993) 125-139.
Maisonneuve et al., "Rapid mapping of two genes for resistance to downy mildew from *Lactuca serriola* to existing clusters of resistance genes," Theor. Appl. Genet. (1994) 89:96-104.
Kuang et. al., "Multiple Genetic Processes Result in Heterogeneous Rates of Evolution within the Major Cluster Disease Resistance Genes in Lettuce," The Plant Cell, vol. 16, 2870-2894 (2004).
Ryder, E.J., "Genetic Studies in Lettuce (*Lactuca sativa* L.)," J. Amer. Soc. Hort. Sci. 96(6): 826-828 (1971).
Schittenhelm et al.: "Efficiency of various insects in germplasm regeneration of carrot, onion and turnip rape accessions", Plant Breeding, vol. 116, No. 4, pp. 369-375 (Sep. 1997).
Tadashi Miura: "On the hourly change of the pollinator association found in the Japanese pear, Var. Nijisseiki Orchard in day-time", Bulletin of the Faculty of Agriculture of Shimane University, vol. 16, pp. 159-165 (1982).
Horikawa et al.: "Flower visitors and pests of mango in the hot-house", Memoirs of the Faculty of Agriculture of Kinki University, No. 38, pp. 19-30 (2005).
Escaravage et al.: "Pollination Effectiveness and Pollen Dispersal in a *Rhododendron ferrugineum* (Ericaceae) Population", Plant Biology, vol. 6, No. 5, pp. 606-615 (2004).
Munawar et al.: "Comparative performance of honeybees (*Apis mellifera* L.) and blow flies (Phormia terronovae) in onion (*Allium cepa* L.) seed setting", J. Agric. Res., vol. 49, No. 1, pp. 49-56 (2011).

* cited by examiner

*Primary Examiner* — David H Kruse
(74) *Attorney, Agent, or Firm* — John P. White; Cooper & Dunham LLP

(57) ABSTRACT

The present invention concerns hybrid *Lactuca sativa* seeds which have a male sterile genotype and which are heterozygous for at least one distinct gene which provides plants derived from said seeds with a distinct phenotype. The invention also concerns a method for producing hybrid *Lactuca sativa* seeds, comprising a step for culture, in an enclosed medium, of phenotypically male sterile plants and phenotypically male fertile plants, a step for pollinization by diptera introduced into the closed medium upon flowering of the plants, and a step for harvesting the seeds produced by the male sterile plants.

16 Claims, 7 Drawing Sheets

♀ : "female" plants
♂ : "male" plants

♀ : "female" plants
♂ : "male" plants

```
TGCGTTCCACCACCGAGACTTCGACACCTGGCTGCCCCATTCGAACTACGCCCTGCGTA
GAGATTCGTACGCCCAGCGTACGTGCGAGGGTGCATCCCTATAAAAGGCATGTGAGACC
TTCGGGTTTGTTGCTCAATATTTCTTCTCTTCTCCCCTTATTCTTTCTATTTCTTGGTA
ATTTATACCCTCGAAACCCCAGTATTATTCTCGAGACCTGAAGCAAGTCCCGAAGCCCT
GAGAATCCCGAGAAGTAAAGTTTTCGAGCCGAAACTCTGCCCGCGAGAATCCCGGTTTT
CAAGAAAGCGTATCGGTTTCACCGAAGAATACTACTCTTAGAGTCGTAGTGTTGTTCGA
TCATCTTTTGATCAAGTGAGTGTATATTCCTTTTCTTCTAACACATAGATACGAAGTAT
TCTCTACAAAATACGTGTTATGTGTTTGTATATTATTTGCTTATTTGAAATAATTGTTG
AATGAATGATTTGTACACGTTCTAAGTTGTATATAAATGTATATATTTTTATCTACTAA
TATGTTGGGTAGAACATGGGTAGAAAGTTGTTGTGAGATGAAATAAAATGATGAGAGGC
CTCGATGTTGATGTTGTTAATCTAGTCATCTAGCGGAGTATGGATGACGATCACGGACT
CTTCCTAGACTGTCCAGTGGAACGCA
```

FIGURE 8

SEQUENCE LISTING

<160> NUMBER OF SEQ ID NOS: 6

<210> SEQ ID NO 1
<211> LENGTH: 10

```
<212> TYPE: DNA
<213> ORGANISM: Artificial
<220> FEATURE:
<223> OTHER INFORMATION: OPBA05 primer

<400> SEQUENCE: 1
tgcgttccac                                                           10

<210> SEQ ID NO 2
<211> LENGTH: 675
<212> TYPE: DNA
<213> ORGANISM: Lactuca sativa

<400> SEQUENCE: 2
tgcgttccac caccgagact tcgacacctg gctgccccat tcgaactacg ccctgcgtag     60
agattcgtac gcccagcgta cgtgcgaggg tgcatcccta taaaaggcat gtgagacctt    120
cgggtttgtt gctcaatatt tcttctcttc tcccttatt ctttctattt cttggtaatt    180
tataccctcg aaacccagt attattctcg agacctgaag caagtcccga agccctgaga    240
atcccgagaa gtaaagtttt cgagccgaaa ctctgcccgc gagaatcccg gttttcaaga    300
aagcgtatcg gtttcaccga agaatactac tcttagagtc gtagtgttgt tcgatcatct    360
tttgatcaag tgagtgtata ttcctttcct tctaacacat agatacgaag tattctctac    420
aaaatacgtg ttatgtgttt gtatattatt tgcttatttg aaataattgt tgaatgaatg    480
atttgtacac gttctaagtt gtatataaat gtatatattt ttatctacta atatgttggg    540
tagaacatgg gtagaaagtt gttgtgagat gaaataaaat gatgagaggc ctcgatgttg    600
atgttgttaa tctagtcatc tagcggagta tggatgacga tcacggactc ttcctagact    660
gtccagtgga acgca                                                    675

<210> SEQ ID NO 3
<211> LENGTH: 24
<212> TYPE: DNA
<213> ORGANISM: Artificial
<220> FEATURE:
<223> OTHER INFORMATION: SCW09-A primer

<400> SEQUENCE: 3
gtgaccgagt agtcttaacc tagt                                           24

<210> SEQ ID NO 4
<211> LENGTH: 24
<212> TYPE: DNA
<213> ORGANISM: Artificial
<220> FEATURE:
<223> OTHER INFORMATION: SCW09-B primer

<400> SEQUENCE: 4
gtgaccgagt gtaacaacgt aaat                                           24

<210> SEQ ID NO 5
<211> LENGTH: 23
<212> TYPE: DNA
<213> ORGANISM: Artificial
<220> FEATURE:
<223> OTHER INFORMATION: B1F primer

<400> SEQUENCE: 5
gagaatagag tcttgtgatg gca                                            23

<210> SEQ ID NO 6
<211> LENGTH: 23
```

```
<212> TYPE: DNA
<213> ORGANISM: Artificial
<220> FEATURE:
<223> OTHER INFORMATION: B1R primer

<400> SEQUENCE: 6
cccgtaagac atggaagttc tct                                        23
```

PRODUCTION OF HYBRID *LACTUCA SATIVA* SEEDS

This application is a §371 national stage of PCT International Application No. PCT/FR2008/000289, filed Mar. 5, 2008, and claims priority of French Patent Application No. 0701589, filed Mar. 5, 2007, the contents of all of which are hereby incorporated by reference into this application.

The present invention relates to hybrid lettuce (*Lactuca sativa*) seeds and to a method for producing said seeds. The invention also relates to hybrid *Lactuca sativa* plants, as well as to cells from hybrid *Lactuca sativa* plants.

Heterosis (or hybrid vigour), homeostasis (the stability of the plant in different environments), the possibility of accumulating genes for resistance to insects, fungi, bacteria or viruses, or adaptation to abiotic stresses such as the resistance to extreme temperatures, i.e. temperatures below 5° C. or above 30° C., or resistance to low light levels, constitute a few reasons for the large scale production of seeds from hybrid plants.

It has in particular been shown that in *Lactuca sativa* (cultivated lettuce), it is impossible or very difficult to accumulate certain resistance genes in a homozygous line, the genes in question being located on the same locus (one on each allele) or on very proximate loci.

Obtaining hybrid F1 cultivated lettuces would be of major interest, particularly in respect of allowing large scale production of hybrids accumulating several co-dominant or dominant genes of agricultural interest carried by the various alleles of the same locus or by very proximate loci.

The *Lactuca* genus includes more than 100 species, including *Lactuca sativa* (cultivated species), *Lactuca saligna* (wild type species), *Lactuca serriola* (wild type species) and *Lactuca virosa* (wild type species).

*Lactuca sativa* is a diploid species (2n=18), largely autogamous, with seed production being 98% by self-pollination. The stamens (male organs) are grouped and form a staminal tube into which the pollen sacs of the anthers open. The pistil (female organ) is constituted by an ovary, a style, and a bifidate stigma. When the flower opens, the style extends inside the staminal tube, and thus the stigma becomes coated with pollen and the plant is self-pollinated. One *Lactuca sativa* plant generally produces 0.5 to 6 grams or even up to 10 grams of seeds depending on the culture conditions, each gram generally including 600 to 1000 seeds.

A conventional technique for the large scale production of hybrid plants consists of cultivating the two varieties used as "parents" close to each other and to use insects for pollinization, one of the parents carrying male sterility to prevent contamination due to self-pollinization. The seeds are then harvested from the male sterile parent.

This technique can accumulate genes of interest present in the homozygous form in each of the parents while retaining homogeneity of the parcel, the F1 generation having a 100% homogenous phenotype at the harvest stage (before the flowers open).

It has been observed that it is very difficult to produce cultivated hybrid lettuces (*Lactuca sativa*) on a large scale using that technique. This is because the *Lactuca sativa* flower only opens once for just a few hours, for example one to four hours, at a time during the day (early morning) when the usual pollinating insects such as certain species of bee (*Apis mellifera*) or bumble bee (*Bombus* spp) are not yet active.

*Lactuca sativa* is also not pollinated by wind.

Thus, identifying a pollinating insect which could be used for the production of hybrid lettuces comes up against a number of problems, in particular:

the period during which the flowers are open is both short and matutinal, making it difficult to identify an insect visiting the flowers;

the flowers only open once, and as a result the selected pollinating insect must be an insect visiting the flowers every day in order to be certain that a maximum number of male sterile flowers are pollinated.

Further, the production of F1 hybrids necessitates the provision of a "male" line and a "female" line. The "female" line may be obtained by dint of manual castration of the plant. However, in the case of the lettuce, because each flower only opens once and for a very short period (a few hours), that method is difficult to carry out on a commercial scale because it would necessitate a great deal of labour.

The "female" line may also be obtained by introducing a genetic (or nuclear) or cytoplasmic type of sterility manifesting itself by an absence of anthers, empty anthers or non-viable pollen. This sterility is transmitted to descendants partially in the case of nuclear (or genetic) sterility or completely in the case of cytoplasmic sterility.

In their work, Goubara and Takasaki (Appl Entomo Zool 38(4), 571-581, 2003 [1] carried out experiments under field and enclosure conditions aimed at identifying potential pollinating insects which could be used for the production of hybrid *Lactuca sativa* lettuces. Of the 22 insects observed (21 species of bee and one nectar-feeding fly species, *syrphidae eristalis tenax*), the bee *Lasioglossum villosulum trichopse* was observed to be the best potential pollinator.

Goubara and Takasaki (Appl Entomo Zool 39(1); 163-169, 2004 [2]) also carried out small scale hybridization trials between a lettuce carrying a male sterility gene and a male-fertile lettuce in an enclosed medium in the presence of the bee lagioglossum villosulum trichopse. The authors state they obtained hybrid F1 lettuces but in a very low yield.

At the present time, no other hybrid *Lactuca sativa* production experiment using a pollinating insect, is known of.

Today, no F1 hybrid lettuce variety is produced at a commercial scale.

In the context of the present invention, the following terms have the following meanings:

cultivated lettuce means the species *Lactuca sativa*. Five principal cultivated lettuce cultigroups exist (see FIG. 1): *Lactuca sativa* var. *angustana* (asparagus lettuce); *Lactuca sativa* var. *capitata* (butterhead lettuce); *Lactuca sativa* var. *crispa* (batavia or Iceberg lettuce); *Lactuca sativa* var. *longifolia* (Romaine lettuce) and *Lactuca sativa* var. *acephala* (frisee lettuce, cutting lettuce). The invention encompasses the use of each of these various types of lettuce.

Pollinization means transporting pollen from the anther to the stigma of the same flower or another flower. This sexual system is the preferred mode of reproduction of plants with flowers (angiosperms and gymnosperms). It allows the grain of pollen to reach the stigma then to form, through the style, a pollen tube reaching to the ovule in order to fertilize it.

Self-pollinization means pollinization of an individual or a biotype using its own pollen, the resulting individuals being termed self-pollinated.

The term autogamous denotes the capacity of a plant to self-pollinate, the two gametes being derived from the same individual.

Allogamous denotes the phenomenon whereby the flowers of an individual are fertilized by pollen from one or more other individuals.

Pollinating insect means an insect (including bees, butterflies, diptera or certain coleopterae) which, in exploring the flowers (for example when searching for nectar) rub against the stamens, thereby harvesting a few grains of pollen which it subsequently leaves on another flower.

Locus means the position occupied by a gene or an allele on a chromosome.

Alleles are variations within a species of a gene located at a given chromosomal position (locus). Different alleles of a gene give rise to different expressions of a trait.

Cluster means two or more genes positioned close to each other on the same chromosome. Clusters of resistance genes identified in the lettuce have in particular been described by Kesseli et al [12].

Dominant gene means a gene which provides a phenotype whether present on two chromosomes of a pair or on only one.

Recessive gene means a gene which only provides a phenotype when it is present on each of two homologous chromosomes.

Co-dominance means the property of two allelic genes to express one and the other of the phenotypic characters they determine. In a heterozygous subject carrying two co-dominant allelic genes, the genotype will be expressed completely in the phenotype as regards the information carried by these genes.

Heterozygote means a cell or an individual which possesses two distinct allelic genes on a predetermined locus of the same pair of chromosomes.

Homozygote means a cell or an individual which possesses two identical allelic genes on a predetermined locus of the same pair of chromosomes.

The term hybrid means the product of a cross between individuals of different genetic constitution, preferably from the same species.

F1 hybrid means the first generation from a cross between individuals with a different genetic constitution. As a consequence, F1 hybrids are heterozygous for at least one gene.

Backcrossing means crossing between a hybrid and one of its parents.

Cultivar means a variety.

Genotype means all of the genetic material carried by an individual and which constitutes its heritage.

Phenotype designates the set of apparent morphological or functional characters of an individual which corresponds both to the expressed portion of the genotype and to phenomena determined by the external medium.

The term phenotype of agricultural interest means a phenotype derived, for example, from a cross between two homozygous genotypes, with interesting characteristics from an agricultural standpoint, such as the accumulation of resistance to various pathogens or insects, hybrid vigour (i.e. the mean level of a hybrid trait being more than the mean of the two parents), homeostasis, the capacity to adapt to abiotic stress, morphological characteristics such as colour, shape, the flexible or rigid nature of the leaves, the nutrient composition or the taste qualities of the plant.

The term heterosis or hybrid vigour means the phenomenon wherein a F1 hybrid is significantly superior to its best parent in respect of one or more characters, especially as regards vigour.

Homeostasis means the capacity of a plant to adapt to its environment or even to several environmental characteristics.

Sterile male means a plant which is incapable of reproducing by self-pollinization because of sterility of the male elements of the flowers. As an example, the pollen may be non-functional or there may be structural anomalies in the male reproductive organs, for example in the tapetum.

Cytoplasmic male sterility means sterility which is transmitted homogeneously by the mother by cytoplasmic type heredity.

Nuclear (or genetic) male sterility means sterility by Mendelian heredity carried by the DNA of the nucleus which may be either under the dependence of a recessive gene or under the dependence of a dominant gene.

Monogenic male sterility means male sterility carried by a single gene.

Plurigenic male sterility means male sterility carried by a plurality of genes.

Resistance means the capacity of a variety to restrict the growth and development of a predetermined pathogen or pest and/or the damage it causes, compared with sensitive varieties, under similar environmental and pressure conditions for that pathogen or pest. These varieties can, however, express some symptoms of the disease or some damage in the case of high pressure of that pathogen or pest.

Standard or high resistance means the capacity of a variety to strongly restrict the growth and development of a predetermined pathogen or pest under normal pressure conditions thereof, compared with sensitive varieties. These varieties may, however, express symptoms or damage in the case of high pressure of that pathogen or pest.

Intermediate or moderate resistance means the capacity of a variety to restrict the growth and development of a predetermined pathogen or pest but which can express more symptoms or damage compared with high/standard resistance varieties. The intermediate resistance varieties show symptoms or damage which is less severe than that observed for sensitive varieties under similar environmental and/or pressure conditions for the pathogen or pest.

Molecular marker means a specific fragment of DNA which can be identified in the complete genome of an individual and which can be used to localize a gene of interest or to verify whether an individual has inherited one particular characteristic from a parent organism. It may or may not be a coding sequence. In genetic crossing, the gene of interest will generally remain linked to the molecular marker. Detection of the molecular marker then means that individuals presenting the gene of interest can be selected without it being necessary to know the sequence of that gene.

In the agronomic field, using molecular markers means that plants can be tested rapidly during selection, to keep those which have the desired characteristics. In certain cases, the presence of markers associated with a trait renders certain tests or phenotypical observations unnecessary. In particular, using a specific molecular marker for a gene for male sterility, preferably a dominant gene for male sterility, allows early selection of male sterile plants before flowering. This selection means that male fertile plants which could form part of the population of plants used as parents assumed to be "female" (male sterile) for the production of hybrid seeds, for example in the case in which a dominant gene for male sterility is used, can be eliminated, and as a result can reduce the risk of contamination linked to self-fertilization of these male fertile plants.

The present invention concerns seeds, plants and cells from hybrid *Lactuca sativa* plants, characterized in that they have a male sterile genotype and are heterozygous for at least one gene not involved in male sterility and endowing the plant with a detectable phenotype.

The male sterility carried by the seeds, plants or cells from *Lactuca sativa* plants may be of nuclear or cytoplasmic origin. In the case in which it is cytoplasmic, the sterility is transmitted by the female parent. It is often due to an interaction between the mitochondria present in the cytoplasm and the nuclear genes. Cytoplasmic male sterility is characterized by the appearance of descendents with a 100% male sterile phenotype in the absence of a gene which restores fertility in the genome of the male parent. Male fertility may be restored in the descendents by the presence of a fertility restoring gene (Rf) in the genome of the "male" parent.

More particularly, the invention concerns the case in which the male sterile genotype involves at least one nuclear gene and in which the seed, cell or plant is heterozygous for the gene or genes at the origin of the male sterility.

Nuclear male sterility is caused by one or more genes for male sterility transmitted by the DNA of the nucleus, this gene or genes possibly being dominant or recessive.

These genes for male sterility include the dominant nuclear gene Ms7 described by Ryder (J Am Soc Hort Sci 96(6), 826-828, 1971 [8]). The male sterile plants are heterozygotes, Ms7 ms7. The fertile plants are homozygotes, ms7 ms7. Obtaining dominant Ms7Ms7 homozygotes is still difficult, if not impossible. Further, according to Ryder, the dominant trait of this male sterility constitutes a problem to using this gene for the production of hybrid lettuces. A sample of *Lactuca sativa* seeds obtained using the method of the present invention, deposited at the NCIMB (NCIMB Ltd., Ferguson Building, Craibstone Estate, Bucksburn, Aberdeen, A21 9YA, Scotland, UK) on 13 Feb. 2007 with accession number NCIMB 41470, constitutes a source of the Ms7 gene. Further, the molecular marker RAPD BA05-675 (SEQ ID NO: 2) developed by the inventors is of particular interest in assisting the selection of male sterile lettuce plants Ms7, because it allows a molecular test to be carried out at an early stage before flowering in order to identify the male sterile plants which will be used for the next cross. Detection of this marker the sequence of which is shown in FIG. 8 allows a male sterile plant to be identified on average in 96% of cases, taking all lettuce typologies together (Table 18).

Three recessive genes for male sterility, ms1, ms2 and ms3, have also been identified by Lindqvist (Heriditas 46 :387-470, 1960 [3]), and three others, ms4, ms5 and ms6, by Ryder (Proc. Am. Soc. Hort. Sci 83:585-595, 1963 [6], Proc. Am. Soc. Hort. Sci 91:366-368, 1967 [7]). However, in his study published in 1979 (Leafy Salad Vegetables, p 30 [9]), Ryder declares that since the sterility genes ms1, ms2, ms3, ms4, ms5, ms6 and Ms7 are all nuclear, it is not very probable that they could be used to produce F1 hybrids. Despite this, the inventors have successfully obtained hybrid seeds, plants and cells using a male sterility of nuclear origin.

Nuclear male sterility may be plurigenic or monogenic. In the case in which it is plurigenic, it may, for example, be obtained using a complex of recessive genes, for example by accumulating the ms1, ms2 and ms3 genes cited above. Preferably, the invention concerns the case in which the male sterility is monogenic.

Nuclear male sterility may be dominant or recessive. In particular, the invention concerns the case in which the male sterility is dominant monogenic. More particularly still, the invention concerns the case in which the male sterility is provided by the dominant Ms7 gene cited above.

Preferably, the genome of the seeds, plants or cells of the invention comprises a double strand DNA sequence of 650 to 700 nucleotides, for example 655 to 695, 660 to 690, 665 to 685, 670 to 680, 673 to 677 nucleotides, or 674, 675 or 676 nucleotides, wherein the 5' ends of each of the two strands commence with the sequence "5' TGCGTTCCAC 3'" (SEQ ID NO: 1). In accordance with a preferred embodiment, the genome of the seeds, plants or cells of the invention comprises the nucleotide sequence illustrated in FIG. 8 (SEQ ID NO: 2) or a sequence derived from this sequence in which 1 to 10, preferably 1 to 5 or more preferably 1 to 3 nucleotides have been replaced by others, deleted or added.

The invention preferably concerns the case in which the detectable phenotype conferred by the heterozygous gene or genes is a phenotype of agricultural interest, such as resistance to various pathogens or insects, hybrid vigour (or heterosis), homeostasis (stability of the plant in different environments), adaptation to abiotic stress such as extreme temperatures or low light levels, a yield which is higher than that of varieties from which a hybrid derives, morphological characteristics such as colour, shape, size, the flexible or rigid nature of the leaves, the nutrient composition or the taste qualities of the plant.

Further, the inventors have observed that surprisingly, hybrid plants derived from seeds of the invention derived from various crosses between different lettuces, cultivated in the winter period and in a temperate region, grew more quickly, reached maturity an average of 7 to 10 days earlier than parent plants cultivated under the same conditions. It was also observed that the homogeneity of intraparcel development of F1 hybrids (on stock of approximately 30 plants per parcel) was higher than that of parcels of lines (parent plants). In other words, the number of plants presenting a tardy or advanced development compared with all of the plants from the same parcel was much smaller for parcels of F1 hybrids than for parcels from line varieties. As a consequence, these characteristics of F1 hybrids not only can shorten the lettuce production cycles but also condense the harvest into a shorter period.

The phenotype of agricultural interest may in particular be provided by one or more genes for standard or intermediate resistance to an infection by a virus, a bacterium, an insect or a fungus, and more particularly still one of the following fungi: *Bremia lactucae, Fusarium oxysporum, Sclerotinia minor* or *sclerotorum, Botrytis cinerea, Rhizictonia solani, Microdochium panattonianum, Verticiulium dahliae, Erysiphe chicocearum* or *Pithium tracheiphilum*, —to one of the following insects: *Nasonovia ribisnigri, Myzus persicae, Macrosiphum euphorbia*, Nematodes *pratylenchus* or *meloidogyne*, leafminers: *Liriomyza huidobrensis* or *Pemphigus busarius*; to one of the following bacteria: *pseudomonas, xanthomonas* or *rhizomonas*; or to one of the following viruses: LMV (lettuce mosaic virus), TSWV (tomato potted wilt virus), "Big vein" (composed of LBVV (lettuce big vein virus) and MILV (miratiori lettuce virus)), TBSV (tomato bushy stunt virus), LNSV (lettuce necrotic stunt virus), TuMV (turnip mosaic virus), CMV (cucumber mosaic virus) or BWYV (beet western yellows virus).

In the case in which the phenotype of agricultural interest is provided by one or more genes for standard or intermediate resistance to an infection by a virus, a bacterium, an insect or a fungus, the or said genes for standard or intermediate resistance providing this phenotype may in particular be selected from the genes for resistance to bremia Dm10, R17, Dm5, Dm8, R36, R37 (genes located on cluster 1 of *Lactuca sativa*), Dm1, Dm2, Dm3, Dm6, Dm14, Dm15, Dm16, Dm18 (genes located on cluster 2 of *Lactuca sativa*), Dm4, Dm7, Dm11, R38 (genes located on cluster 4 of *Lactuca sativa*); or the Tu gene for resistance to TuMV located on cluster 1; the Nr gene for resistance to Nasonovia located on cluster 2; or from the genes mol.1 and mol.2 for resistance to LMV located on cluster 4. Clusters 1, 2 and 4 cited above have been defined by Michelmore R. W. (Plant Pathol, 1987, vol. 36, no 4: 499-514 [4], Theor. Appl. Genet., 1993, vol. 85, No 8: 985-993 [5])

More particularly, the phenotype of agricultural interest may be provided by one or more genes for standard or intermediate resistance to one of the principal diseases affecting lettuce, *Bremia lactucae*, a fungus which causes a whitish, powdery down on the inner face of the limb. In addition, *Bremia* is highly capable of adapting, which results in the appearance of new races which are capable of overturning the resistances already introduced by the plant breeders into the varieties.

More preferably, the invention concerns the case in which the seeds, plants or cells of *Lactuca sativa* plants are heterozygous for at least two genes which are not involved in male sterility and provide the plant with a detectable phenotype. More preferably still, the two genes or more providing the plant with a detectable phenotype are located on the same cluster, for example on a cluster of resistance genes such as cluster 1, 2 or 4 of *Lactuca sativa*.

The invention also pertains to a population of hybrid *Lactuca sativa* seeds with a male sterile genotype, and heterozygous for at least one gene not involved in male sterility and providing plants derived from said seeds with a detectable phenotype, optionally having the additional characteristics of the seeds described above, such that said population comprises at least $10^5$ seeds, preferably at least $10^6$, and more preferably at least $10^7$ seeds.

In the case in which the seeds are obtained by crossing two *Lactuca sativa* plants, one of which (the "female" parent) carries a nuclear male sterility provided by one or more dominant genes, and the plants used as the "female" parents are themselves derived from a cross, the plants used as the "female" parents are necessarily heterozygous for the sterility gene. In fact, for them to be homozygous for the dominant male sterility gene or genes, the two plants from which the plants used as "female" parents are derived by crossing would themselves have to be carriers of a gene for male sterility; but if that were the case, a cross between these two plants would be impossible.

As a consequence, because of the phenomenon of chromosome segregation during meiosis, the population of seeds of the invention derived from a cross between two types of *Lactuca sativa* plants one of which (the "female" parent) is a carrier of a nuclear male sterility provided by one or more dominant genes, is composed of *Lactuca sativa* seeds carrying a dominant gene or genes for male sterility, and seeds not carrying this or these genes. In the case in which the male sterility carried by the "female" parent is monogenic and dominant, the proportion of sterile male seeds is generally at least 40%.

The present invention came about following the observation by the inventors that although diptera are not routine pollinating insects for *Lactuca sativa* flowers, and moreover are not known to feed on their nectar, these insects, in particular the species *Calliphora vomitaria*, *Calliphora erythrocephala*, and *Lucilia Caesar*, when introduced in excess numbers into an enclosed medium, act as pollinators for *Lactuca sativa*.

In addition, the present invention pertains to the use of insects of the diptera in order to carry out pollinization, in an enclosed medium, of male sterile *Lactuca sativa* plants by male fertile plants, in particular with a view to obtaining hybrid *Lactuca sativa* plants. Preferably, the male sterile *Lactuca sativa* plants used have a male sterility carried by a single dominant gene, preferably the male sterility Ms7 cited above. The fertile male plants used are preferably *Lactuca sativa* plants and more preferably a cultivar.

The enclosed medium of the invention may in particular be a glasshouse, a cage or a tunnel, preferably with a surface area of more than 30 $m^2$, more preferably more than 300 $m^2$, for example 30 to 1500 $m^2$ or 50 to 1000 $m^2$. The height of the closed medium is normally in the range 2 m to 4 m, preferably in the range 2.5 m to 3.5 m, for example 3m. It may in particular include means for ventilation, watering, temperature control and light level control. Preferably, said closed medium is an enclosure which is hermetically sealed to insects.

The diptera used must preferably be present in a concentration of at least 100 diptera per $m^2$, preferably at least 250 diptera per $m^2$, for example 100 to 1000 diptera per $m^2$. The concentration may also be determined as the number of diptera per $m^3$, and is preferably at least 25 diptera per $m^3$, preferably more at least 50 diptera per $m^3$, preferably again at least 75 diptera per $m^3$, for example 25 to 500 diptera per $m^3$ or 75 to 250 diptera per $m^3$.

The present invention also pertains to a method for obtaining hybrid *Lactuca sativa* seeds, comprising:
- a step for cultivating, in an enclosed medium, phenotypically male sterile *Lactuca sativa* plants used as "female" parents and phenotypically male fertile *Lactuca sativa* plants used as "male" parents, close to each other, one of the two parents having an additional characteristic of being homozygous for a gene providing it with a detectable phenotype other than male sterility, the other parent not carrying this gene;
- a step for pollinization by diptera introduced into the enclosed medium on flowering of the plants in a concentration of more than 100 diptera per $m^2$, preferably at least 250 diptera per $m^2$; and
- a step for harvesting the seeds produced by the sterile male plants.

Preferably, the second parent is also homozygous for at least one gene providing it with a detectable phenotype other than male sterility, not carried by the other parent. Preferably, said closed medium is an enclosure which is hermetically sealed to insects.

The best results have been observed when the diptera are in excess, and in addition their concentration is preferably greater than 400 diptera per $m^2$, and more preferably more than 500 diptera per $m^2$.

The diptera may be introduced at the egg stage, larva stage, pupa stage or adult stage. Preferably, they are introduced in the form of pupae.

The diptera used are preferably brachycera, for example cyclorhapha brachycera, more preferably brachycera from the Muscidae or Calliphorides family, for example *Calliphora vomitaria*, *Calliphora erythrocephala* or *Lucilia Caesar*.

A better yield is normally obtained if the diptera introduction is repeated at least once a week, preferably twice a week, over at least 3 to 4 weeks.

Similarly, a better yield is normally obtained if the number of male sterile plants in the closed medium is larger than the number of male fertile plants. The number of male sterile plants in the closed medium is, for example, at least 2000, and the number of male fertile plants is, for example, at least 1000.

The implementation of the method of the invention necessitates that flowering of the two parents happens at the same time. This can be achieved by selecting for this trait or by using appropriate culture practices.

Preferably, the male sterility of the plants used as the female parents is monogenic, dominant and nuclear, and more preferably provided by the gene Ms7.

Preferably, the genome of the plants used as the female parents comprises a double strand DNA sequence of 650 to 700 nucleotides, for example 655 to 695, 660 to 690, 665 to 685, 670 to 680, 673 to 677 nucleotides, or 674, 675 or 676 nucleotides, the 5' ends of each of the two strands starting with the sequence "5' TGCGTTCCAC 3'" (SEQ ID NO: 1). In accordance with a preferred embodiment, the genome of the plants used as "female" plants comprises the nucleotide sequence illustrated in FIG. 8 (SEQ ID NO: 2) or a sequence derived from this sequence in which 1 to 10, preferably 1 to 5 or more preferably 1 to 3 nucleotides have been replaced by others, deleted or added.

As explained above, because of the phenomenon of chromosomal segregation during meiosis, it is not possible to obtain a homogeneous population of plants used as "female" plants carrying a dominant gene for male sterility by conventional crossing techniques. As a consequence, in the case in which a dominant gene for male sterility is used, the plants used as female parents may be obtained by a method comprising:

- a step for crossing between *Lactuca sativa* plants which are heterozygous for a dominant gene for nuclear male sterility and male fertile *Lactuca sativa* plants not carrying sterility genes;
- a step for culture of seeds obtained from said cross; and
- a step for eliminating plants having a male fertile phenotype.

The step for eliminating plants having a male fertile phenotype may, for example, be carried out manually, based on a visible characteristic allowing male sterile *Lactuca sativa* plants to be distinguished from male fertile *Lactuca sativa* plants. As an example, in the case of a sterility linked to the Ms7 gene, sorting may be carried out by exploiting the fact that the flower-heads of male sterile plants remain open longer than those of male fertile plants, and that male sterile plants do not have pollen.

In accordance with an alternative embodiment, the step for eliminating plants with a male fertile phenotype is carried out by detecting the absence of a specific molecular marker for the male sterility dominant gene in a sample of each of the plants. It may, for example, be a RAPD (random amplification of polymorphic DNA) marker with a length of approximately 675 base pairs (for example 650 to 700, 655 to 695, 660 to 690, 665 to 685, 670 to 680, 673 to 677, 674, 675 or 676 base pairs) wherein one 5' end of each of the two strands starts with the sequence "5' TGCGTTCCAC 3'" (SEQ ID NO: 1), such as the marker BA05-675 (SEQ ID NO: 2) developed by the inventors or a SCAR (sequenced characterized amplified region marker), a CAPS (cleaved amplified polymorphic sequence) marker or any other marker generally designated as a STS (sequence tagged site) developed using this RAPD marker. In a preferred embodiment, detecting the presence or absence of a specific molecular marker for a dominant gene for male sterility is carried out before flowering of the plants used as female parents, preferably at an early stage of growth of the plants, for example at the 1 to 5 leaf stage, or more preferably at the 1 to 2 leaf stage.

Preferably, the molecular marker used can detect male sterile plants with a sensitivity of at least 70%, 75%, 80%, 85%, 95%, 98% or 99%, or even 100%, the sensitivity being defined as the ratio between the number of male sterile plants having the molecular marker (true positives) and the sum of the number of true positives and the number of male sterile plants not having the molecular marker (false negatives) (see Table 17).

Preferably again, the molecular marker used can detect male sterile plants with a specificity of at least 70%, 75%, 80%, 85%, 95%, 98% or 99%, or even 100%, the specificity being defined as the ratio between the number of male fertile plants not presenting the molecular marker (true negatives) and the sum of the number of true negatives and the number of male fertile plants having the molecular marker (false positives) (see Table 17).

The TSW (thousand seed weight) of seeds obtained using the method of the invention is generally at least 10%, or even at least 20% or even at least 30% greater than the TSW of the seeds obtained by self-fertilization of the male fertile *Lactuca sativa* plants used as the "male" parents.

The invention also concerns a population of seeds which can be obtained using the method described above, and comprising at least $10^5$ seeds, preferably $10^6$ seeds and more preferably $10^7$ seeds.

BRIEF DESCRIPTION OF THE DRAWINGS

FIG. 8: 5'-3' nucleotide sequence for BA05-675 marker associated with Ms7 male sterility in lettuce, *Lactuca sativa* (SEQ ID NO: 2).

EXAMPLES

Example 1

Obtaining Hybrid Lettuce Seeds

The male sterile *Lactuca sativa* plants used in the various trials described below as "female" parents carried the Ms7 sterility gene. These plants were derived from a 5th generation backcross (BC5) of a greenhouse butterhead lettuce carrying the Ms7 gene (X Girelle 94-9538-1) which may be obtained from various research organizations such as INRA, USDA, etc.

The Ms7 gene is dominant, and so a cross between two plants carrying the Ms7 gene is impossible. As a consequence, plants having a male sterility phenotype are necessarily heterozygous for the Ms7 gene and can only be obtained by crossing between Ms7/ms7 (sterile) and ms7/ms7 (fertile) plants.

As a result, a purification step is required to eliminate the male fertile plants. This latter step was rendered possible because Ms7/ms7 plants do not have pollen and the flower-heads of Ms7/ms7 plants remain open longer than those of ms7/ms7 plants.

Trial 1

In the context of the first trial:
- 450 greenhouse butterhead *Lactuca sativa* plants from a $3^{rd}$ generation backcross (BC3) of Ms7 butterhead lettuce with butterhead lettuce from the Nacre/Cambria Dm18/R38 cultivar (Dm18 resistance genes from cluster 2 and R38 from cluster 4), a combination which is sensitive to *Bremia lactucae* race 24 (B124), were used as "female" parents (approximately half of them being sterile males); and
- 100 *Lactuca sativa* plants from the BRA Dm18/R37 greenhouse butterhead cultivar (Dm18 resistance genes from cluster 2 and R37 from cluster 1), a combination which is resistant to B124, were used as the "male" parents.

The two genitors flowered at exactly the same time, which meant that fertilization could be as homogeneous as possible.

Figure 1:
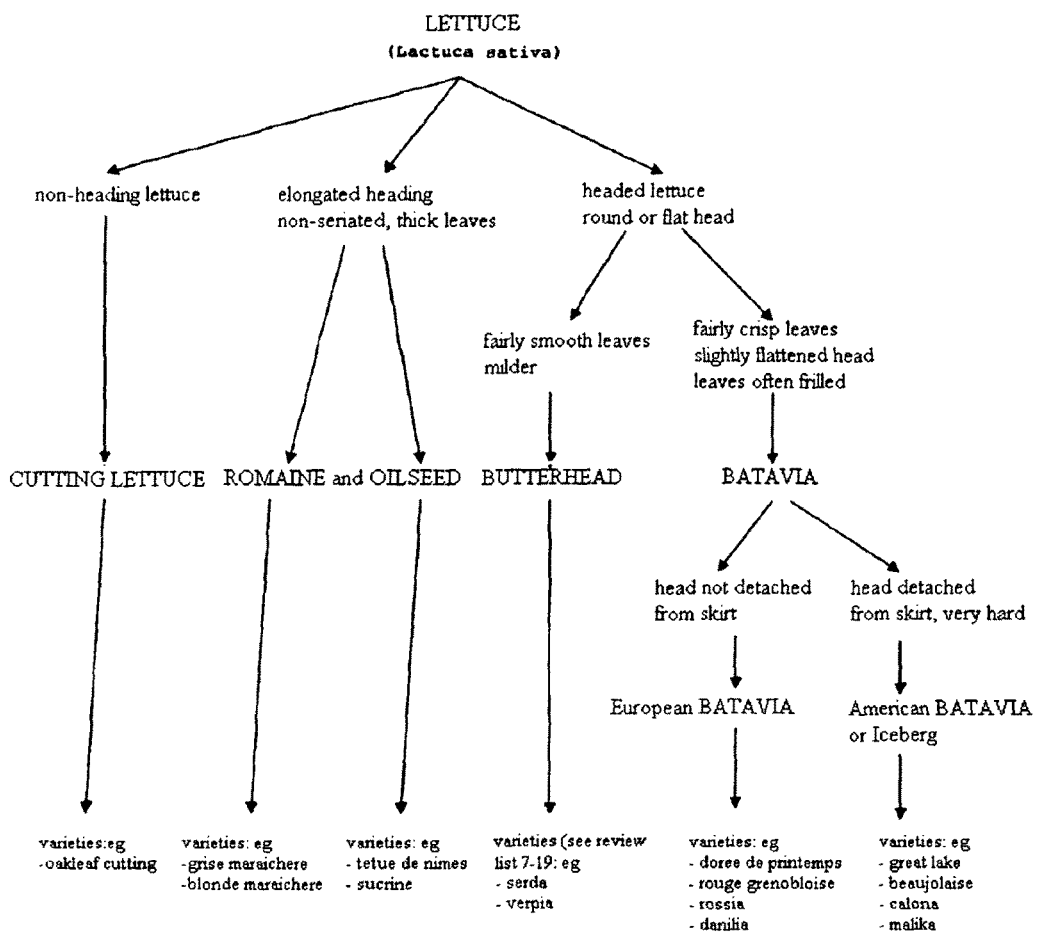
FIG. 1: Genealogy of *Lactuca sativa*.
Figure 2:
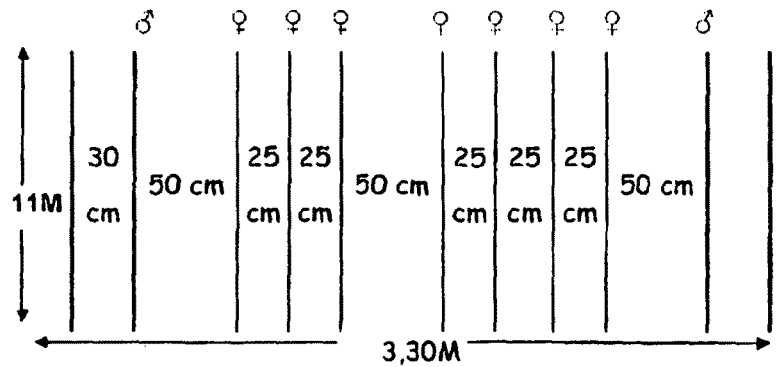
FIG. 2: Disposition of lettuces used as "male" and "female" parents during trial 1.

The plants were disposed in an enclosure which was hermetically sealed to insects of 36 m² (Dutch type greenhouse with humidity and temperature control, 11 m×3.30 m) as follows (see FIG. 2):
- the plants used as "male" parents were disposed in two rows along the edges of the closed enclosure, the plants being spaced apart by 20 cm; and
- the plants used as "female" parents were disposed in seven rows between the two rows of "male" plants at a distance of 50 cm therefrom, the plants being spaced apart by 15 cm and the rows by 25 cm.

Sowing was carried out in week 13 and planting out in week 16.

Because of the dominant nature of the Ms7 gene, a step for purification (elimination) of the plants used as female parents with a male fertile phenotype was necessary. This step was carried out manually in weeks 26 and 27, exploiting the fact that Ms7/ms7 plants do not have pollen and that the flower-heads of the Ms7/ms7 (male sterile) plants stay open longer than those of the ms7/ms7 plants (male fertile).

Of the 450 plants used as female parents, 217 were male sterile and were effectively used.

Two types of insects from the diptera order and the Calliphorides family were used as pollinating insects:
- *Calliphora vomitaria* and *Calliphora erythrocephala* flies, known as "maggots" (also known as bluebottle or blowflies) operating at 15-20° C.; and
- *Lucilia Caesar* flies known as "pinkies" (also known as greenbottles) operating at 20-25° C.

The pollinating insects were added bi-weekly during weeks 28 to 31 in a concentration of 300 ties per m² per addition.

The male sterile plants ("female" parents) and male fertile plants ("male" parents) also used as the self-fertilization control were harvested in week 33.

The plants were dried, threshed then the seeds were passed through a column of pulsed air to complete cleaning and eliminate the residual light waste, and calibrated for length and width.

A sample of 2500 seeds obtained during trial 1 was deposited on 13 Feb. 2007 at NCIMB (NCIMB Ltd., Ferguson Building, Craibstone Estate, Bucksburn, Aberdeen, A21 9YA, Scotland, UK) with accession number NCIMB 41470.

Trial 2

A similar second trial was carried out on a larger scale in an enclosure which was hermetically sealed to insects of 336 m² (length: 56 m; width: 6 m, height: 3 m).

In the context of this second trial:
- 3000 greenhouse butterhead *Lactuca sativa* plants derived from a $4^{th}$ generation backcross (BC4) of Ms7 butterhead lettuce with butterhead lettuce from the Nacre/Cambria Dm18/R38 cultivar, *Bremia* (a combination which is sensitive to 8124) were used as "female" parents (approximately half of them being male sterile); and
- 1500 parallel plants from a BRA Dm18/R37 greenhouse butterhead cultivar resistant to B124 were used as the "male" parents.

Figure 3:
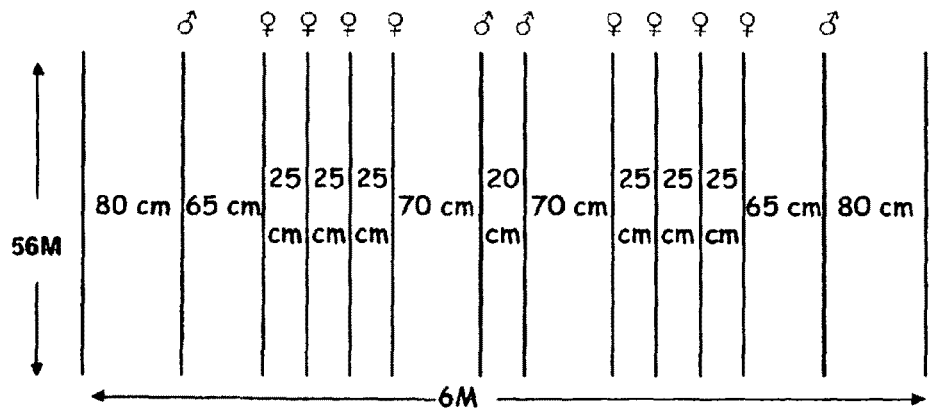
FIG. 3: Disposition of lettuces used as "male" and "female" parents during trial 2.

The plants were disposed in a sealed enclosure as follows (see FIG. 3):
- the plants used as "male" parents were disposed in four rows: one row along each edge of the closed enclosure (at 80 cm) and two rows in the centre (spaced apart by 20 cm), the plants being staggered in disposition and with a 15 cm spacing; and
- the plants used as "female" parents were disposed in eight rows between the rows of fertile male plants at a distance of 65 and 70 cm therefrom, the plants being spaced apart by 15 cm and the rows by 25 cm.

Sowing was carried out in week 12 and planting out in week 16.

In similar manner to trial 1, a step for purification (elimination) of the plants used as female parents with a male fertile phenotype was necessary. This step was carried out manually in weeks 25 and 26 exploiting the fact that Ms7/ms7 plants do not have pollen and that the flower-heads of Ms7/ms7 (sterile male) plants stay open longer than those of ms7/ms7 plants (male fertile).

Of the 3000 plants used as female parents, 1250 were male sterile and were effectively used.

16 ms7/ms7 plants (male fertile) were conserved, however, during purification, and self-fertilized in a hermetically sealed enclosure constituted by a net which did not allow insects to pass through, in order to be used as the self-fertilization control.

The pollinating insects used were the same as those used in trial 1.

The pollinating insects were added weekly during weeks 25 to 29 in a concentration of 1100 flies per m² per addition.

At the same time, 10 male fertile plants (male parents) and the 16 fertile ms7/ms7 plants conserved during the purification step were self-fertilized in a hermetically sealed enclosure constituted by a net which did not allow insects to pass through, in order to act as self-fertilization controls.

The male sterile plants ("female" parents), as well as the 10 male fertile plants (male parents) and the 16 fertile ms7/ms7 plants conserved during the purification step used as self-fertilization controls were harvested in week 33.

The plants were dried, threshed then the seeds were passed through a column of pulsed air to complete cleaning and eliminate residual light waste, and calibrated for length and width.

A sample of the seeds obtained was sown and the resistance of the plants obtained to B124 was tested in accordance with the official GEVES protocol (Groupe d'Etude et de contrôle des Variétés et des Semences [Varieties and Seeds Study and Monitoring Group]). It transpired that the plants were resistant to B124.

Results of Trials 1 and 2

The results of trials 1 and 2 are shown in the tables below.

TABLE 1

Comparison of weights of seeds harvested during trials 1 and 2

| | Plants | Harvested weight (g) | Weight (g/plant) |
|---|---|---|---|
| Trial 1 | Self-fertilization control (91 "male" parent plants) | 2000 | 22 |
| | F1 MS7 (217 "female" parent plants pollinated by flies) | 730 | 3.36 |
| Trial 2 | Self-fertilization control 1 (10 "male" parent plants) | 83 | 8.3 |
| | Self-fertilization control 2 (16 male fertile ms7/ms7 "female" parent plants) | 288 | 18 |
| | F1 MS7 (1170 "female" parent plants pollinated by flies) | 7730 | 6.61 |

TABLE 2

Comparison of gauging of hybrid seeds and seeds derived from the self-fertilization controls produced during trials 1 and 2

| | Plants | Gauge | Weight in g after cleaning | % | % useful | % rejected |
|---|---|---|---|---|---|---|
| Trial 1 | Self-fertilization control (91 "male" parents) | >3.5-4.5< | 1774 | 89.10 | 89 | 10 |
| | | >4.5 | 200 | 10.05 | | |
| | | <3.5 | 17 | 0.85 | | |
| | | total | 1991 | | | |
| | Ms7 F1 (217 "female" parent plants pollinated by flies) | >3.5-4.5< | 620 | 93.83 | 94 | 6 |
| | | >4.5 | 28.5 | 4.31 | | |
| | | <3.5 | 12.3 | 1.86 | | |
| | | total | 660.8 | | | |
| Trial 2 | Self-fertilization control 1 (10 "male" parent plants) | >3.5-4.5< | 67.5 | 88.12 | 88 | 12 |
| | | >4.5 | 7.6 | 9.92 | | |
| | | <3.5 | 1.5 | 1.96 | | |
| | | total | 76.6 | | | |
| | Self-fertilization control 2 (16 female ms7/ms7 "female" parent plants) | >3.5-4.5< | 228.3 | 81.48 | 81 | 19 |
| | | >4.5 | 50.3 | 17.95 | | |
| | | <3.5 | 1.6 | 0.57 | | |
| | | total | 280.2 | | | |
| | Ms7 F1 (1170 "female" parent plants pollinated by flies) | >3.5-4.5< | 7730 | 98.85 | 99 | 1 |
| | | >4.5 | 0 | 0 | | |
| | | <3.5 | 90 | 1.15 | | |
| | | total | 7820 | | | |

TABLE 3

Comparison of TSW (thousand seed weight) of hybrid seeds and seeds from self-fertilization controls produced during trials 1 and 2

| | Plants | TSW measurement 1 (g) | TSW measurement 1 (g) | TSW measurement 1 (g) | Mean TSW (g) |
|---|---|---|---|---|---|
| Trial 1 | Self-fertilization control (91 "male" parent plants) | 0.9569 | 0.9603 | 0.954 | 0.9571 |
| | F1 Ms7 (217 "female" parent plants pollinated by flies) | 1.3609 | 1.3587 | 1.3484 | 1.356 |
| Trial 2 | Self-fertilization control 1 (10 "male" parent plants) | 1.0784 | 1.0721 | 1.0745 | 1.075 |
| | Self-fertilization control 2 (16 male fertile ms7/ms7 "female" parent plants) | 1.1144 | 1.1182 | 1.112 | 1.1149 |
| | F1 Ms7 (1170 "female" parent plants pollinated by flies) | 1.4039 | 1.4036 | 1.4065 | 1.4047 |

Discussion

During the first trial, 730 grams of seeds were obtained from 217 male sterile *Lactuca sativa* plants (female parent), namely a yield of 3.36 grams per plant, corresponding to a ratio of 15.30% of the self-fertilized control (male parent).

During the second trial, 7.730 kg of seeds were thus obtained from 1170 male sterile *Lactuca sativa* plants (female parent), namely a yield of 6.60 grams per plant, corresponding to a ratio of 50% of the mean of two self-fertilized controls ("male" parents and ms/ms male fertile "female" parents, conserved during purification and fertilized under insect-hermetic seal).

During the second trial, the amount of useful seeds after gauging the F1 hybrids was more than 10% of the self-fertilized control.

During the two trials, the TSW (thousand seed weight) of the F1 hybrid was 20% to 30% greater than the self-fertilized control.

The plants obtained from the seeds obtained in the second trial were resistant to B124.

Trials 3 to 8

Six similar trials were launched at the same time with different types of butterhead and batavia lettuces in insect proof 3.3 m×1.1 m cages each containing 8 *Lactuca sativa* plants used as "female" parents (with 50% male sterile derived from a back-cross between *Lactuca sativa* plants carrying the Ms7 gene and fertile *Lactuca sativa* plants) and 4 male fertile *Lactuca sativa* plants used as "male" parents placed in a ventilated greenhouse.

Sowing was carried out in week 22, planting out in week 27, sorting of male sterile from male fertile "female" plants at the onset of flowering in week 31, flies were added in weeks 32, 33 and 34 in an amount per week over three weeks, i.e. approximately 100 flies/m$^2$; harvesting was carried out in week 37.

Results of Trials 3 to 8

Cage 1: CHARLIN(8/12624)*CHARLIN (butterhead)
    1 female plant: 9.20 g
    1 male plant: 28.30 g Cage 2: CHARLIN(BC/77)*CHARLIN (butterhead)
    1 female plant: 5.45 g
    1 male plant: 19.40 g Cage 3: BRA 68/12588 (greenhouse apple lettuce)*BRA 68/12588
    6 female plants:
        plant 1: 7.00 g
        plant 2: 2.00 g
        plant 3: 5.20 g
        plant 4: 3.40 g
        plant 5: 9.60 g
        plant 6: 8.40 g
        mean: 5.9 g/plant
    1 male plant: 34.40 g Cage 4: BRA 68/12588*BRA 68/12588
    4 female plants:
        plant 1: 11.95 g
        plant 2: 7.15 g
        plant 3: 15.90 g
        plant 4: 11.90 g
        mean: 11.25 g/plant
    1 male plant: 29.00 g Cage 5: BVA 68/12553 (greenhouse batavia lettuce)*BVA 68/12553
    5 female plants:
        plant 1: 3.50 g
        plant 2: 1.30 g
        plant 3: 2.20 g
        plant 4: 1.70 g
        plant 5: 4.20 g
        mean: 3.30 g/plant
    1 male plant: 3.60 g Cage 6: BVA 68/12553*BVA 68/12553
    3 female plants:
        plant 1: 4.60 g
        plant 2: 3.20 g
        plant 3: 3.70 g
        mean: 3.80 g/plant
    1 male plant: 23.40 g Discussion The "female" parent production means were from 3.3 g to 11.2 g/plant, the batavia typology (BVA 68/12553) having a substantially lower yield (approximately 3.5 g/plant) compared with a butterhead typology (Charlin, BRA 68/12588) at approximately 8.5 g/plant, which gives rise to the thought that typology plays a major role in the final yield.

Trial 9

A new production trial was carried out in small insect proof cages measuring 0.40 m in diameter, placed in a ventilated greenhouse on open ground.

Sowing was carried out in week 22, re-potting in week 25, the male sterile "female" plants were sorted from the male fertile plants at the onset of flowering in week 30, planting out in week 31, flies were added in weeks 32, 33 and 34 at one addition per week for 3 weeks, i.e. approximately 100 flies/m$^2$, and harvesting was carried out in week 35.

Results

The results obtained are summarized in Tables 4 and 5 below.

TABLE 4

Production of seeds by "male" and "female" parents, Charlin (greenhouse butterhead)

| Female Charlin parent | Wt, g | Male Charlin parent | Wt, g |
|---|---|---|---|
| 1 | 3.3 | 1 | 1.65 |
| 2 | 0.76 | 2 | 1.7 |
| 3 | 0.44 | 3 | 3 |
| 4 | 1.1 | 4 | 1.18 |
| 5 | 4.18 | 5 | 1.9 |
| 6 | 2.7 | 6 | 2.95 |
| 7 | 1.72 | 7 | 1.9 |
| 8 | 1.78 | 8 | 2.3 |
| 9 | 1.92 | | |
| Mean | 1.99 | Mean | 2.0725 |

TABLE 5

Production of seeds by "male" and "female" parents, BVA 68/12553 (batavia)

| Female BVA 68/12553 (batavia) parent | Wt, g | Male BVA 68/12553 (batavia) parent | Wt, g |
|---|---|---|---|
| 1 | 1.1 | 1 | 1.45 |
| 2 | 1.17 | 2 | 0.95 |
| 3 | 1.2 | 3 | 2 |
| 4 | 1.48 | 4 | 1.6 |
| 5 | 0.66 | 5 | 1.27 |
| 6 | 0.69 | 6 | 3 |
| 7 | 0.55 | 7 | 1.8 |
| 8 | 1.22 | 8 | 1.9 |
| 9 | 0.75 | 9 | 1.26 |
| 10 | 1.3 | 10 | 2.3 |
| 11 | 1.57 | 11 | 1.15 |
| 12 | 0.52 | 12 | 1.4 |
| 13 | 0.55 | | |
| Mean | 0.98 | Mean | 1.67 |

Discussion

The results were satisfactory in that the mean production obtained for the batavia lettuce (BVA 68/12553) was approximately 1 g/plant as opposed to 1.7 g/plant for the self-fertilized control, and the mean production obtained for the greenhouse butterhead lettuce (Charlin) was approximately 1 g/plant, about the same as the self-fertilized control.

Trial 10: Dm3/Dm18 Accumulation by Hybrid Combination

F1 hybrid lettuces accumulating two dominant genes, Dm3 and Dm18, for *Bremia lactucae* resistance, respectively race 24 (B124) and race 23 (B123) belonging to cluster 2 and situated at the same locus, were obtained using the method described in the trials described above.

The plants used as "female" parents (06/30443: MS7/21NACRExDEVONIAxCAMBRIA) were carriers of the resistance genes Dm18 and R38. The plants used as "male" parents were greenhouse butterhead lettuces carrying the resistance gene Dm3 (BC: 06/30443*Rex or BC:06/30443*Melina).

The following five crosses were carried out:

06/30443/01 (MS7/21xNACRExDEVONIAxCAMBRIA-01) Dm18/R38*Rex Dm3

06/30443/10 (MS7/21xNACRExDEVONIAxCAMBRIA-10) Dm18/R38*Rex Dm3

06/30443/02 (MS7/21xNACRExDEVONIAxCAMBRIA-02) Dm18/R38*Melina Dm3

06/30443/03 (MS7/21xNACRExDEVONIAxCAMBRIA-03] Dm18/R38*Melina Dm3

06/30443/04 (MS7/21xNACRExDEVONIAxCAMBRIA-04] Dm18/R38*Melina Dm3.

The seeds derived from these five crosses were sown and inoculation tests on leaf disks and molecular labelling were carried out on the F1 plants, as well as on the "male" (Rex/Melina) and "female" parents.

I Inoculation Tests on Leaf Disks

Equipment: The plant material was constituted by 1.5 cm diameter leaf disks in a number of 5 disks per plant and per race, 10 plants per origin and two *Bremia lactucae* races (B124 which attacks the Dm18/R38 accumulation and to which Dm3 confers resistance and B123 which attacks the Dm3/R38 accumulation and to which Dm18 confers resistance). Thus, 80 plants in total were tested over two races.

Technique: The leaf disks were inoculated by spraying sporocysts with races of *Bremia* B123 and B124 separately.

1/Removal of leaf disks: Five leaf disks per plant were removed and deposited on a double thickness of moist blotting paper. Each dish contained 6 lines of disks to be tested and one line of sensitive control.

2/Inoculation: The quantity of inoculum necessary for inoculating 6 dishes of disks leaf was 11 ml. A stock solution of Tween 80 was prepared using 4 drops of Tween 80 added to 100 ml of demineralized water. The quantity of extraction solution for the volume of inoculum was 5 ml of Tween stock solution per 100 ml of inoculum. The inoculum was produced by detaching the sporocysts in tap water supplemented by 5% of Tween 80 stock solution. The sporocysts were removed in an amount of 1 plant/ml of inoculum, to obtain a concentration of sporocysts of close to $10^8$ spores/ml. Filtration was carried out by passing the solution through a gauze into a 250 ml beaker.

3/Spraying: Inoculation was carried out on the day the leaf disks were taken. The volume of the inoculum solution was measured then the deployed dishes were inoculated. The inoculum was sprayed homogeneously in fine droplets over the whole surface of each disk. The dishes were hermetically sealed and incubated in a unit at 15° C., with 14 h daylight, 10 hours night for 7 days.

Results: The results of the inoculations are shown in Tables 6 to 13 below (S=sensitive; R=resistant). The hybrids from the various crosses were resistant to the two races B123 and B124, indicating the presence of the two genes Dm18 and Dm3 from cluster 2.

TABLE 6

"Female" 30443 (Dm18/R38) plants: MS7/21xNACRExDEVONIAxCAMBRIA: B123 resistant and B124 sensitive

| GENOTYPE | PLANT | B123 | B124 |
|---|---|---|---|
| 06/30443 | 2 | R | S |
| 06/30443 | 3 | R | S |
| 06/30443 | 4 | R | S |
| 06/30443 | 5 | R | S |
| 06/30443 | 6 | R | S |
| 06/30443 | 7 | R | S |
| 06/30443 | 8 | R | S |
| 06/30443 | 9 | R | S |
| 06/30443 | 10 | R | S |

TABLE 7

"Male" Melina (Dm3) plants: B123 sensitive and B124 resistant (test on 10 plants)

| GENOTYPE | PLANT | B123 | B124 |
|---|---|---|---|
| MELINA | 1 | S | R |
| MELINA | 2 | S | R |
| MELINA | 3 | S | R |
| MELINA | 4 | S | R |
| MELINA | 5 | S | R |
| MELINA | 6 | S | R |
| MELINA | 7 | S | R |
| MELINA | 8 | S | R |
| MELINA | 9 | S | R |
| MELINA | 10 | S | R |

TABLE 8

06/30443/02 * Melina (Dml8/R38 * Dm3) cross = MS7/2IxNACRExDEVONIAxCAMBRIA-02 * MELINA

| GENOTYPE | PLANT | B123 | B124 |
|---|---|---|---|
| 06/30443/02 * MELINA | 2 | R | R |
| 06/30443/02 * MELINA | 3 | R | R |
| 06/30443/02 * MELINA | 4 | R | R |
| 06/30443/02 * MELINA | 5 | R | R |
| 06/30443/02 * MELINA | 6 | R | R |
| 06/30443/02 * MELINA | 7 | R | R |
| 06/30443/02 * MELINA | 8 | R | R |
| 06/30443/02 * MELINA | 9 | R | R |
| 06/30443/02 * MELINA | 10 | R | R |

TABLE 9

06/30443/03 * Melina (Dml8/R38 * Dm3) cross = MS7/2IxNACRExDEVONIAxCAMBRIA-03 * MELINA

| GENOTYPE | PLANT | B123 | B124 |
|---|---|---|---|
| 06/30443/03 * MELINA | 2 | R | R |
| 06/30443/03 * MELINA | 3 | R | R |
| 06/30443/03 * MELINA | 4 | R | R |
| 06/30443/03 * MELINA | 5 | R | R |
| 06/30443/03 * MELINA | 6 | R | R |
| 06/30443/03 * MELINA | 7 | R | R |
| 06/30443/03 * MELINA | 8 | R | R |
| 06/30443/03 * MELINA | 9 | R | R |
| 06/30443/03 * MELINA | 10 | R | R |

TABLE 10

06/30443/04 * Melina (Dml8/R38 * Dm3) cross = MS7/2IxNACRExDEVONIAxCAMBRIA-03 * MELINA

| GENOTYPE | PLANT | B123 | B124 |
|---|---|---|---|
| 06/30443/04 * MELINA | 2 | R | R |
| 06/30443/04 * MELINA | 3 | R | R |
| 06/30443/04 * MELINA | 4 | R | R |
| 06/30443/04 * MELINA | 5 | R | R |
| 06/30443/04 * MELINA | 6 | R | R |
| 06/30443/04 * MELINA | 7 | R | R |
| 06/30443/04 * MELINA | 8 | R | R |
| 06/30443/04 * MELINA | 9 | R | R |
| 06/30443/04 * MELINA | 10 | R | R |

TABLE 11

"Male" Rex (Dm3) plants: B123 sensitive and B124 resistant (test on 10 plants)

| GENOTYPE | PLANT | B123 | B124 |
|---|---|---|---|
| REX/1 | 1 | S | R |
| REX/2 | 2 | S | R |
| REX/3 | 3 | S | R |
| REX/4 | 4 | S | R |
| REX/5 | 5 | S | R |
| REX/6 | 6 | S | R |
| REX/7 | 7 | S | R |
| REX/8 | 8 | S | R |
| REX/9 | 9 | S | R |
| REX/10 | 10 | S | R |

TABLE 12

06/30443/01 * Rex (Dml8/R38 * Dm3) cross = MS7/21xNACRExDEVONIAxCAMBRIA-01 * REX

| GENOTYPE | PLANT | B123 | B124 |
|---|---|---|---|
| 06/30443/01 * REX | 2 | R | R |
| 06/30443/01 * REX | 3 | R | R |
| 06/30443/01 * REX | 4 | R | R |
| 06/30443/01 * REX | 5 | R | R |
| 06/30443/01 * REX | 6 | R | R |
| 06/30443/01 * REX | 7 | R | R |
| 06/30443/01 * REX | 8 | R | R |
| 06/30443/01 * REX | 9 | R | R |
| 06/30443/01 * REX | 10 | R | R |

TABLE 13

06/30443/10 * Rex (Dml8/R38 * Dm3) cross = MS7/21xNACRExDEVONIAxCAMBRIA-10 * REX

| GENOTYPE | PLANT | B123 | B124 |
|---|---|---|---|
| 06/30443/02 * REX | 2 | R | R |
| 06/30443/02 * REX | 3 | R | R |
| 06/30443/02 * REX | 4 | R | R |
| 06/30443/02 * REX | 5 | R | R |
| 06/30443/02 * REX | 6 | R | R |
| 06/30443/02 * REX | 7 | R | R |
| 06/30443/02 * REX | 8 | R | R |
| 06/30443/02 * REX | 9 | R | R |
| 06/30443/02 * REX | 10 | R | R |

II Molecular Labelling

Using 2 molecular markers allows to demonstrate the accumulation of two closely linked genes (located on the same locus) which are dominant and for resistance to two *Bremia lactucae* strains in *Lactuca sativa*.

Method:

1/Plant material: The plant material was constituted by 1.5 cm diameter leaf disks, one disk per plant. The DNA from 5 to 10 plants per genotype (i.e. 50 plants in total) was obtained by CTAB/chloroform extraction followed by taking up into suspension in a solution of TE 0.1× in a concentration of 5 ng/µl.

2/Genotyping: The SCW09 and B1 markers described by Maisonneuve et al [10] and Kuang et al [11] were used to genotype the 50 plants (Table 14). The PCR conditions are described in Table 15.

The PCR cycles for SCW09 and B1 were respectively as follows:

94° C./30s-94° C./1 min, 60° C./1 min, 72° C./2 min; 40 cycles-72° C./5 min-4° C.;

94° C./30s-94° C./1 min, 63° C./1 min, 72° C./2 min; 40 cycles-72° C./5 min-8° C.

The SCW09 marker underwent enzymatic digestion with the TaqI enzyme before the migration step (buffer 1×, BSA 1× and TaqI 1U). Electrophoresis was carried out on 2% (SCW09) or 1.5% (B1) agarose gel in a TBE 1× buffer for 1 h (B1) or 1 h 30 (SCW09) with a constant voltage of 220 V. The electrophoretic profiles were revealed by staining with ethidium bromide (ETB) under a UV lamp.

TABLE 14

Characteristics of SCW09 and B1 markers

| Locus | Test | Type | Primer | Sequence | Tm | GC % | Polymorphism |
|---|---|---|---|---|---|---|---|
| SCW09 | Dm18 | CAPS | SCW09-A | GTGACCGAGTAGTCTTAACCTAGT (SEQ ID NO: 3) | 61.0 | 46% | Co-dominant |
|  |  |  | SCW09-B | GTGACCGAGTGTAACAACCTAAAT (SEQ ID NO: 4) | 59.3 | 42% |  |
| B1 | Dm3 | SCAR | B1F | GAGAATAGAGTCTTGTGATGGCA (SEQ ID NO: 5) | 58.9 | 43% | Dominant |
|  |  |  | B1R | CCCGTAAGACATGGAAGTTCTCT (SEQ ID NO: 6) | 60.6 | 48% |  |

TABLE 15

PCR conditions for SCW09 and B1 markers

| Chemical products | SCW09 | B1 |
|---|---|---|
| $H_2O$ | Qsp 20 µl | Qsp 20 µl |
| Buffer | 1X | 1X |
| $MgCl_2$ | 2.5 mM | 1.5 mM |
| dNTP | 0.2 mM | 200 µM |
| Forward primer | 0.04 µM | 100 nM |
| Reverse primer | 0.04 µM | 100 nM |
| Taq polymerase, Cetus | 1 u | 1 U |
| DNA | 5 µl | 5 µl |

Results

Figure 4:
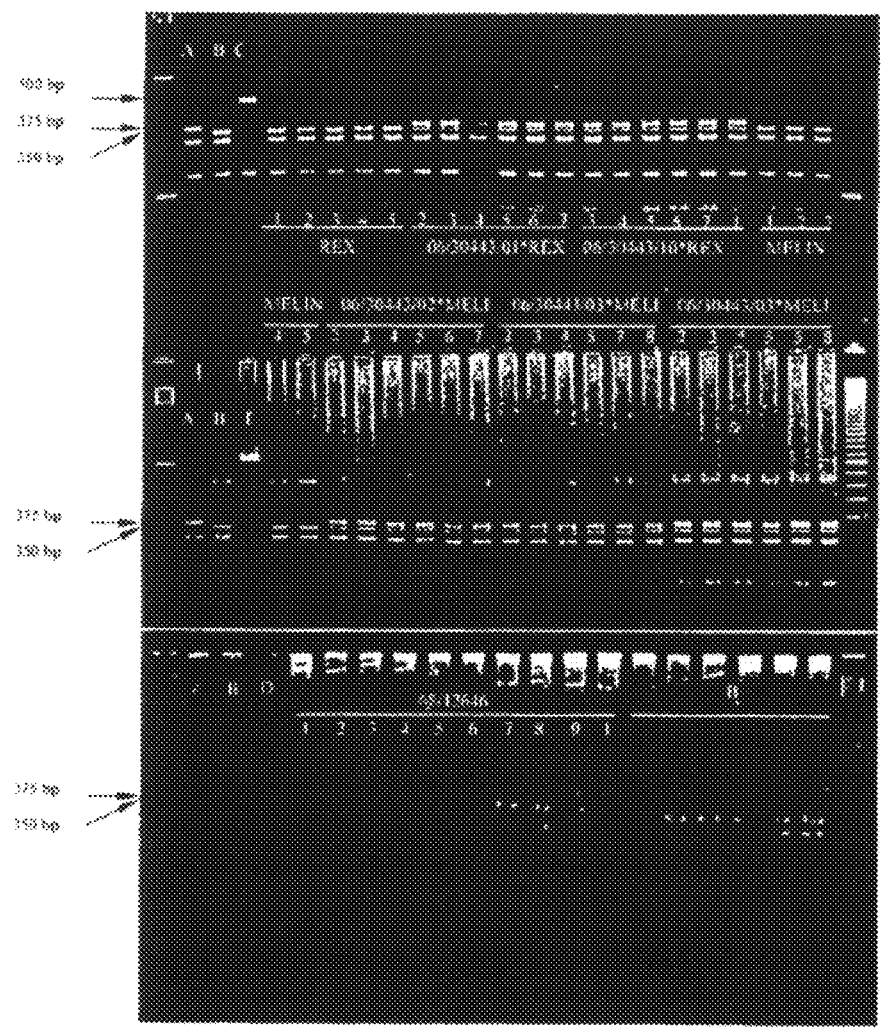
FIG. 4: Genotyping of 50 hybrid plants from trial 10: amplification profile of molecular marker SCW09 after digestion with TaqI. The SCW09 marker labels the Dm6 and Dm18 genes for resistance to *Bremia lactucae*. A=Dm18+/Dm18+ control, B=Dm18−/Dm18− control; C=Dm6+ control; D=not digested by TaqI.
Figure 5:
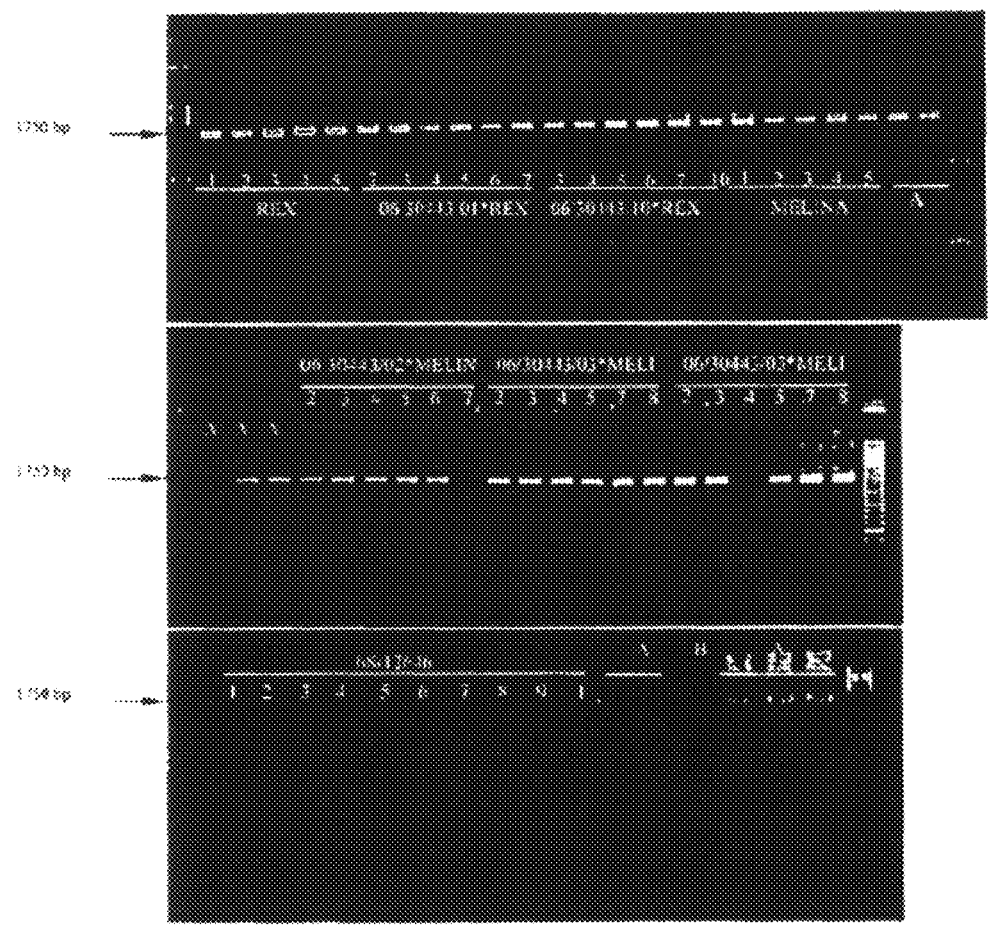
FIG. 5: Genotyping of 50 hybrid plants from trial 10: amplification profile of molecular marker B1 which labels the Dm3 gene for resistance to *Bremia lactucae*. A=Dm3+ control, B=Dm3− control.

The results are shown in Table 16 and FIGS. 4 and 5. The genotypes REX and MELINA had Dm18−/Dm18− and Dm3+ profiles. The 06/30443 genotype had a Dm18+/Dm18+ and Dm3− profile. The set of crosses with one or other of the parents (REX or MELINA) had Dm18+/Dm18− and Dm3+ profiles, i.e. resistant for Dm18 and Dm3.

TABLE 16

Results of genotyping with SCW09 and B1 markers (S = sensitive; R = resistant)

| GENE NO | GENOTYPE | PLANT | B123 (Dm18) | B124 (Dm3) | Dm3 (B1) | DM18 (SCW09) |
|---|---|---|---|---|---|---|
| G02766 | REX | 1 | S | R | Dm3+ | Dm18−/Dm18− |
| G02767 | REX | 2 | S | R | Dm3+ | Dm18−/Dm18− |
| G02768 | REX | 3 | S | R | Dm3+ | Dm18−/Dm18− |
| G02769 | REX | 4 | S | R | Dm3+ | Dm18−/Dm18− |
| G02770 | REX | 5 | S | R | Dm3+ | Dm18−/Dm18− |
| G02771 | 06/30443/01*REX | 2 | R | R | Dm3+ | Dm18+/Dm18− |
| G02772 | 06/30443/01*REX | 3 | R | R | Dm3+ | Dm18+/Dm18− |
| G02773 | 06/30443/01*REX | 4 | R | R | Dm3+ | Dm18+/Dm18− |
| G02774 | 06/30443/01*REX | 5 | R | R | Dm3+ | Dm18+/Dm18− |
| G02775 | 06/30443/01*REX | 6 | R | R | Dm3+ | Dm18+/Dm18− |
| G02776 | 06/30443/01*REX | 7 | R | R | Dm3+ | Dm18+/Dm18− |
| G02777 | 06/30443/10*REX | 3 | R | R | Dm3+ | Dm18+/Dm18− |
| G02778 | 06/30443/10*REX | 4 | R | R | Dm3+ | Dm18+/Dm18− |
| G02779 | 06/30443/10*REX | 5 | R | R | Dm3+ | Dm18+/Dm18− |
| G02780 | 06/30443/10*REX | 6 | R | R | Dm3+ | Dm18+/Dm18− |
| G02781 | 06/30443/10*REX | 7 | R | R | Dm3+ | Dm18+/Dm18− |
| G02782 | 06/30443/10*REX | 10 | R | R | Dm3+ | Dm18+/Dm18− |
| G02783 | MELINA | 1 | S | R | Dm3+ | Dm18−/Dm18− |
| G02784 | MELINA | 2 | S | R | Dm3+ | Dm18−/Dm18− |
| G02785 | MELINA | 3 | S | R | Dm3+ | Dm18−/Dm18− |
| G02786 | MELINA | 4 | S | R | Dm3+ | Dm18−/Dm18− |
| G02787 | MELINA | 5 | S | R | Dm3+ | Dm18−/Dm18− |
| G02788 | 06/30443/02*MELINA | 2 | R | R | Dm3+ | Dm18+/Dm18− |
| G02789 | 06/30443/02*MELINA | 3 | R | R | Dm3+ | Dm18+/Dm18− |
| G02790 | 06/30443/02*MELINA | 4 | R | R | Dm3+ | Dm18+/Dm18− |
| G02791 | 06/30443/02*MELINA | 5 | R | R | Dm3+ | Dm18+/Dm18− |
| G02792 | 06/30443/02*MELINA | 6 | R | R | Dm3+ | Dm18+/Dm18− |
| G02793 | 06/30443/02*MELINA | 7 | R | R | Dm3+ | Dm18+/Dm18− |
| G02794 | 06/30443/03*MELINA | 2 | R | R | Dm3+ | Dm18+/Dm18− |
| G02795 | 06/30443/03*MELINA | 3 | R | R | Dm3+ | Dm18+/Dm18− |
| G02796 | 06/30443/03*MELINA | 4 | R | R | Dm3+ | Dm18+/Dm18− |
| G02797 | 06/30443/03*MELINA | 5 | R | R | Dm3+ | Dm18+/Dm18− |
| G02798 | 06/30443/03*MELINA | 7 | R | R | Dm3+ | Dm18+/Dm18− |
| G02799 | 06/30443/03*MELINA | 8 | R | R | Dm3+ | Dm18+/Dm18− |
| G02800 | 06/30443/04*MELINA | 2 | R | R | Dm3+ | Dm18+/Dm18− |
| G02801 | 06/30443/04*MELINA | 3 | R | R | Dm3+ | Dm18+/Dm18− |
| G02802 | 06/30443/04*MELINA | 4 | R | R | Dm3+ | Dm18+/Dm18− |
| G02803 | 06/30443/04*MELINA | 5 | R | R | Dm3+ | Dm18+/Dm18− |
| G02804 | 06/30443/04*MELINA | 7 | R | R | Dm3+ | Dm18+/Dm18− |
| G02805 | 06/30443/04*MELINA | 8 | R | R | Dm3+ | Dm18+/Dm18− |
| G02806 | 06/30443 | 1 | R | S | Dm3− | Dm18+/Dm18+ |
| G02807 | 06/30443 | 2 | R | S | Dm3− | Dm18+/Dm18+ |
| G02808 | 06/30443 | 3 | R | S | Dm3− | Dm18+/Dm18+ |
| G02809 | 06/30443 | 4 | R | S | Dm3− | Dm18+/Dm18+ |
| G02810 | 06/30443 | 5 | R | S | Dm3− | Dm18+/Dm18+ |
| G02811 | 06/30443 | 6 | R | S | Dm3− | Dm18+/Dm18+ |
| G02812 | 06/30443 | 7 | R | S | Dm3− | Dm18+/Dm18+ |
| G02813 | 06/30443 | 8 | R | S | Dm3− | Dm18+/Dm18+ |
| G02814 | 06/30443 | 9 | R | S | Dm3− | Dm18+/Dm18+ |
| G02815 | 06/30443 | 10 | R | S | Dm3− | Dm18+/Dm18+ |

Example 2

Identification of a Molecular Marker for the Ms7 Gene

The method for obtaining a molecular marker associated with male sterility Ms7 in *Lactuca sativa* (lettuce) described below is given by way of indication.

1—Construction of Populations for Development of a Marker Linked to Nuclear Male Sterility Ms7 in Lettuce (*Lactuca sativa*)

Two populations with different typologies for lettuce with Ms7 male sterility, were produced by back-crossing. Two recurrent fourth generation populations (BC4) of 200 plants obtained thereby were then phenotyped for the "absence of viable pollen" trait corresponding to the male sterile phenotype. Two phenotypical groups were identified as male fertile (F) or male sterile (S) in a ratio of 1:1.

This ratio confirmed the dominant monogenic nature of the male sterility provided by the heterozygous parent at the Ms7 locus.

2—Extraction of DNA from Lettuce Plants

DNA was extracted using the modified CTAB protocol (Tomas et al., 1989 [20]; Doyle et al., 1990 [15]; Edwards et al., 1991 [16]) using fresh young leaves.

Fresh leaf disks obtained using a 1.5 ml tube were ground in 500 µl of extraction buffer (tris-HCl 0.1M, NaCl 0.7 M, EDTA 10 mM, CTAB 1%, β-mercaptoethanol 1%). The ground material was incubated for 1 h at 65° C. and mixed 2 to 3 times by inversion during incubation.

200 µp of a 24:1 chloroform:isoamyl alcohol solution was then added and mixed by inversion. Ater centrifuging at 6000 rpm for 10 minutes at 20° C., 400 µl of supernatant was recovered and mixed with 400 µl of isopropanol.

After 1 h at −20° C., the mixture was centrifuged at 6000 rpm for 10 minutes, at 4° C. The tubes were emptied. The DNA residue attached to the bottom of the tube was allowed to dry in air for 12 h.

The DNA was taken up into suspension in 200 µl of a solution of TE 0.1×(tris-HCl 1 mM, EDTA 0.1 mM). The final concentration was measured by Lambda DNA-HindIII Digest assay on 1% agarose gel.

3—Investigation of RAPD Marker Associated with Ms7 Male Sterility in *Lactuca sativa* Using the BSA (Bulk Segregant Analysis) Method With the aim of identifying a molecular marker Ms7 associated with male sterility, RAPD® 10mer kits from Operon Technologies Inc. (Huntsville, Ala. 35805, USA) and the bulk Segregant Analysis method (Michelmore et al., 1991 [17] and Paran et al., 1991 [18]) were used.

Starting from phenotyping of the two BC4 populations described above, two samples of mixtures of 10 plants were produced for the two groups, "male sterile" and "male fertile". 1200 primers (Operon Biotechnologies Inc. (Huntsville, Ala. 35805, USA) of OPA-01 to OPBH-20 were tested using the RAPD technique described by William et al., 1990 [22] and Welsh et al., 1990 [21] for 4 samples per population. The primers revealing a specific band for the "male sterile" samples and having an electrophoresis profile which was easy to read were selected.

The PCR reaction was carried out in a total reaction volume of 25 µl constituted by PCR 1× buffer, 3 mM $MgCl_2$, 200 µM of dNTPs, 400 nM of primer, 1 unit of AmpliTaq (Perkin-Elmer cetus) DNA polymerase. The PCR reaction consisted of several cycles described as follows: 1 step at 94° C. for 30 s; 45 cycles at 94° C. for 1 min then 35° C. for 1 min and finally 72° C. for 2 min and a final elongation step carried out at 72° C. for 5 min, the reaction then being stored at 4° C.

The amplification products were separated on 2% agarose gel under the following electrophoresis conditions: migration buffer TBE IX (tris-borate-EDTA) at 190V for 2 h15.

Figure 6:
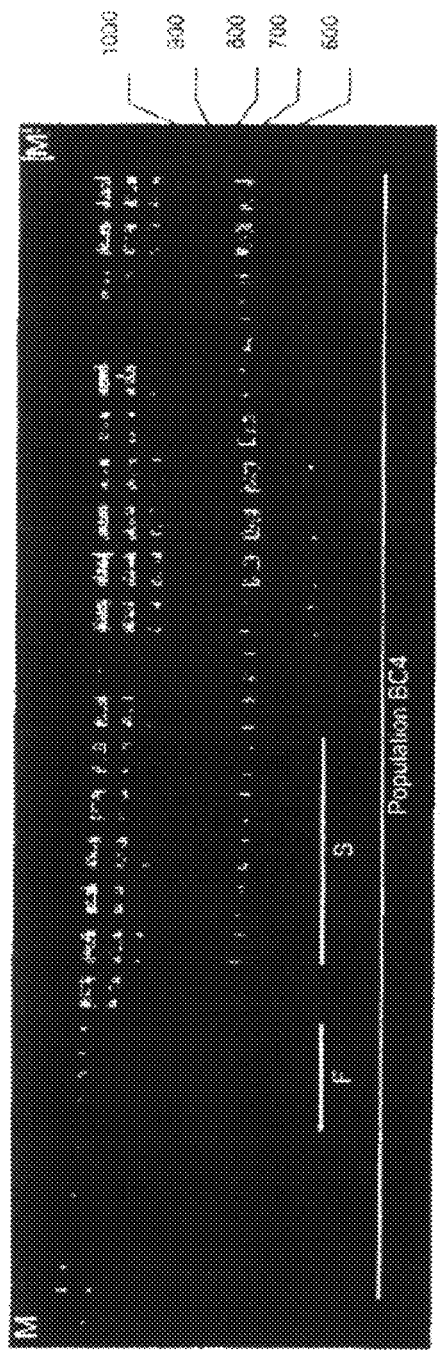
FIG. 6: Electrophoretic profile for OPBA05 primer with the marker BA05-675 (arrow). 1.0% agarose gel electrophoresis for 1 h45 at 190 V. M: 100 by ladder molecular weight marker (Pharmasica Biotech, ref. 27.4001.01)

In order to validate the retained RAPD primers, each of the 200 plants from the two BC4 populations was tested individually for OPBA05 primer having the following sequence: 5' TGCGTTCCAC 3' (SEQ ID NO: 1) to which a marker of 675 bp, BA05-675 (SEQ ID NO: 2) corresponded, which co-segregates with Ms7. The electrophoretic profile obtained for this marker is shown in FIG. 6.

This marker was validated on various typologies of lettuce (batavia, butterhead, iceberg, romaine, oakleaf and lollo rossa) on approximately 25 plants from 12 populations. The test conditions were identical to those described previously for the extraction, amplification and electrophoresis steps.

The computation of the sensitivity and specificity of the RAPD BA05-675 marker gave different values, depending on the typologies, and respective mean values of 96% and 94% (see Tables 17 and 18).

TABLE 17

Detail of computation of predictive values, sensitivity and specificity of retained molecular markers

|  |  | Male Sterile | Male Fertile |  |
|---|---|---|---|---|
| Marker (present [1] or absent [0]) | 1 | Number of true positives (#TP) | Number of false positives (#FP) | Positive predictive value = #TP/(#TP + #FP) |
|  | 0 | Number of false negatives (#FN) | Number of true negatives (#TN) | Negative predictive value = #TN/(#TN + #FN) |
|  |  | SENSITIVITY = #TP/(#TP + #FN) | SPECIFICITY = #TN/(#TN + #FP) |  |

TABLE 18

Results by lettuce typology and mean value of computation of sensitivity (S*) and specificity (F**) for molecular marker BA05-675 associated with Ms7

| | BA05-675 | |
|---|---|---|
| POP | S* | F** |
| BATAVIA | 100% | 100% |
| LOLLO ROSSA | 100% | 100% |
| BUTTERHEAD | 100% | 91% |
| ICEBERG | 95% | 100% |
| ROMAINE | 100% | 71.4% |
| OAKLEAF | 82% | 100% |
| Mean | 96% | 94% |

4—Genetic Mapping of BA05-675 Associated with Ms7 Male Sterility in the *Lactuca sativa* Species Starting from 200 plants from a BC4 population disjointed for ms7 described above, genetic mapping (William et al, 1993 [23]) of the BA05-675 marker associated with Ms7 was carried out using JoinMap®4 (Stam et al, 1996 [19]) and CarteBlanche© (Keygene N P, P O Box 216, 6700 A E Wageningen, The Netherlands). The $X^2$ statistical test verified the zero hypothesis of a Mendelian type 1:1 ratio (test not significant at $p > 0.05$) for the dominant BA05-675 marker (see Table 19). A binding test with a probable ratio (or LOD score) of 3.0 or more allowed this 1.8 cM marker of Ms7 to be mapped (FIG. 6).

TABLE 19

Ratios of molecular segregation marker BA05-675 associated with Ms7 and results of $X^2$ test at 1 ddl using the zero hypothesis for a Mendelian type segregation with ratio 1:1 (F: number of fertile male plants; S: number of sterile male plants)

| Locus | F:S | X2 (1:1) |
|---|---|---|
| BA05-675 | 103:95 | 0.25 |

5—Cloning and sequencing of the RAPD BA05-675 molecular marker associated with male sterility in the *Lactuca sativa* lettuce Starting from the agarose gel electrophoretic profile, the 675 by DNA fragment was isolated and taken up into suspension in a TE buffer (10 mM tris-HCl, 1 mM EDTA) then re-amplified under the PCR conditions described above. The re-amplified isolated fragment was cloned using the commercial PCR®4-TOPO® kit (Invitrogen, Carlsbad, Calif. 92008, USA). After verification of cloning, DNA extractions (Midiprep system) were carried out using a Promega column purification kit (Madison, Wis., USA).

Purified clones concentrated to 75 ng/µl were sequenced by Cogenics (38944 Meylan, France). The sequence for the BA05-675 marker described in FIG. 8 was thus obtained (SEQ ID NO: 2).

6—Results

Figure 7:
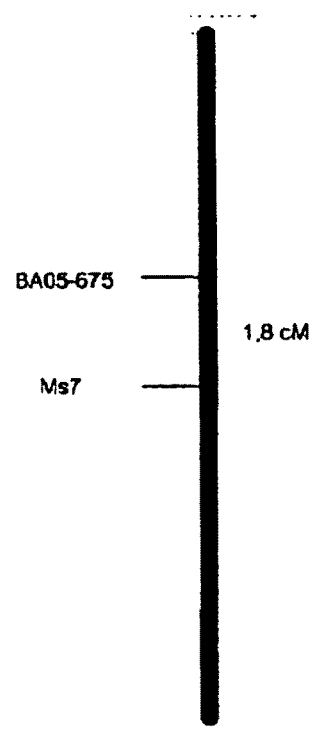
FIG. 7: Mapping of BA05-675 molecular marker associated with Ms7 locus in lettuce, *Lactuca sativa* (distance calculated using Kosambi's function)

The study carried out by the inventors allowed a RAPD marker, BA05-675 (SEQ ID NO: 2) to be defined. Its sequence is shown in FIG. 8, 1.8 cM distant from Ms7 (FIG. 7) and having a mean sensitivity and specificity of 96% and 94% respectively independently of the typology of the lettuce (Table 18). The evaluation of this marker on individual plants from 2

BC4 populations allowed it to be estimated that the mean predictive value (Altman 1994a [13]) for identifying sterile male plants is close to 97%.

Literature

1. Goubara & Takasaki (2003) Flower visitors of lettuce under field and enclosure conditions, Appl. Entomo. Zool. 38(4): 571-581.
2. Goubara & Takasaki (2004) Pollination effects of the sweat bee *Lasioglossum villosulum trichopse* on genic-male lettuce, Appl. Entomo. Zool. 39(1): 163-169, 2004.
3. Lindqvist, K. (1960) Inheritance studies in lettuce, Heriditas 46: 387-470.
4. Michelmore, R. W. et al. (1987) Genetic analysis of factors for resistance to downy mildew in lettuce, Plant Pathol., vol. 36, no 4: 499-514.
5. Michelmore, R. W. et al. (1993) Development of reliable PCR-based markers linked to downy mildew resistance genes in lettuce, Theor. Appl. Genet., vol. 85, No 8: 985-993.
6. Ryder, E. J. (1963) An epistatically controlled pollen sterile in lettuce (*Lactuca sativa* L.), Proc. Am. Soc. Hort. Sci. 96: 826-828.
7. Ryder, E. J. (1967) A recessive male sterile gene in lettuce, Proc. Am. Soc. Hort. Sci 91: 366-368.
8. Ryder, E. J. (1971) Genetic Studies in Lettuce {*Lactuca sativa* L.), J. Amer. Soc. Hort Sci 96(6) 826-828.
9. Ryder, E. J. (1979) Leafy Salad Vegetables, Avi. Pub. Co., page 30.
10. Maisonneuve, B. et al. (1994) Rapid mapping of two genes for resistance to downy mildew from *Lactuca serriola* to existing clusters of resistance genes, Theor. Appl. Genet. 89: 96-104.
11. Kuang H., et al. (2004) Multiple genetic processes result in heterogeneous rates of evolution within the major cluster disease resistance genes in lettuce, The plant cell, Vol. 16, 2870-2894.
12. Kesseli R. V., et al. (1994) Analysis of a detailed linkage map of *Lactuca sativa* (lettuce) constructed from RFLP and RAPD markers, Genetics 136: 1435-1446.
13. Altman D. G., Bland J. M., 1994a. Statistics Notes: Diagnostic tests 1: sensitivity and specificity. British Medical Journal, 308:1552.
14. Altman D. G., Bland J. M., 1994b. Statistics Notes: Diagnostic tests 2: predictive values. British Medical Journal, 30:102.
15. Doyle J. J., and Doyle J. L., 1990. Isolation of plant DNA from fresh tissue. Focus 12, 13-15.
16. Edwards K., Johnstone C. and Thompson C, 1991. A simple and rapid method for the preparation of plant genomic DNA for PCR analysis. Nucleic Acid Res 19:1349.
17. Michelmore R. W., Paran I., Kesseli R. V., 1991. Identification of markers linked to disease-resistance genes by bulked segregant analysis: a rapid method to detect markers in specific genomic regions by using segregating populations. Proc Natl Acad Sci USA 88:9828-9832.
18. Paran I., Kesseli R., Michelmore R. W., 1991. Identification of restriction fragment length polymorphism and random amplified polymorphic DNA markers linked to downy mildew genes in lettuce, using near-isogenic lines Genome 34:1021-1027.
19. Stam P., & J. W. van Ooijen, 1996. JoinMap, version 2.0. Software for the calculation of genetic linkage maps. Ed. CPRO-DLO, 60 pp.
20. Tomas H. T., and Tanksley S. D., 1989. A rapid and inexpensive method for isolation of total DNA from dehydrated plant tissue. Plant Mol Biol Rep 12:106-109.
21. Welsh J, McClelland M., 1990. Fingerprinting genomes using PCR with arbitrary primers. Nucleic Acids Res, 18:7213-7218.
22. Williams J. K. G., Kubelik A. R., Livak K. J., Rafaisky J. A., Tynger S. V., 1990. DNA polymorphism amplified by arbitrary primers are useful as genetic markers. Nucleic Acids Res, 18:6531-6535.
23. Williams J. K. G., Reiter R. S., Young R. M., Scolnik P. A., 1993. Genetic mapping of mutations using phenotypic pools and mapped RAPD markers. Nucleic Acids Res., 21(11): 2697-2702.

The invention claimed is:

1. A method for carrying out pollinization in an enclosed medium of male sterile *Lactuca sativa* plants by male fertile plants, comprising introducing insects of the dipteral order in a concentration of more than 100 diptera per m² or 25 diptera per m³ into said enclosed medium, wherein said insects belong to the *Calliphora* or *Lucilia* genera.

2. A method for obtaining hybrid *Lactuca sativa* seeds, comprising:
   a. culturing, in an enclosed medium, phenotypically male Sterile *Lactuca sativa* plants used as "female" parents and phenotypically male fertile *Lactuca sativa* plants used as "male" parents in proximity to each other, one of the female parents or the male parents being, as a supplemental characteristic, homozygous for a gene which provides it with a detectable phenotype other than male sterility, and the other of the female parents or the male parents not carrying said gene;
   b. pollinating with diptera introduced into the enclosed medium at the time of flowering of the plants in a concentration of more than 100 diptera per m² or more than 25 diptera per m³, wherein said diptera belong to the *Calliphora* or *Lucilia* genera; and
   c. harvesting the seeds produced by the male sterile "female" plants.

3. The method according to claim 2, wherein the other of the female parents or the male parents is also homozygous for at least one gene providing it with a detectable phenotype other than male sterility, not carried by the one of the female parents or the male parents.

4. The method according to claim 2, wherein said diptera are introduced in the form of pupae.

5. The A method according to claim 2, wherein said closed medium is an enclosure which is hermetically sealed to insects.

6. The method according to claim 2, wherein said diptera are *Calliphora vomitaria, Calliphora erythrocephala* or *Lucilia* Caesar.

7. The method according to claim 2, wherein in the enclosed medium, the number of male sterile plants is greater than the number of male fertile plants.

8. The method according to claim 2, wherein in the enclosed medium, the number of male sterile plants is at least 2000, and the number of male fertile plants is at least 1000.

9. The method according to claim 2, wherein introduction of the diptera is renewed at least once a week, over 3 to 4 weeks.

10. The method according to claim 2, wherein the male sterility of the plants used as female parents is of monogenic origin, dominant and nuclear, and wherein the plants used as female parents are obtained by a method comprising:
    a. crossing between *Lactuca sativa* plants which are heterozygous for a dominant nuclear male sterility gene and male fertile Lactuca sativa plants not carrying sterility genes;
    b. culturing the seeds obtained from said cross; and
    c. eliminating the plants having a male fertile phenotype.

11. The method according to claim 10, wherein eliminating the plants having a male fertile phenotype is carried out by detecting, in a sample of each of the plants, the absence of a molecular marker which is specific for the male sterility dominant gene.

12. The method according to claim 10, wherein the male sterility of the plants used as female parents is provided by the Ms7 gene.

13. The method according to claim 2, wherein the genome of the plants used as female parents comprises a double strand DNA sequence of 650 to 700 nucleotides wherein the 5' ends of each of the two strands commences by the sequence TGCGTTCCAC (SEQ ID NO: 1).

14. The method according to claim 1, wherein said insects of the dipteral order are *Calliphora vomitaria, Calliphora erythrocephala* or *Lucilia* Caesar.

15. The method according to claim 2, wherein said concentration of diptera introduced is more than 250 mdiptera per m² or more than 50 diptera per m³.

16. The method according to claim 15, wherein said concentration of diptera introduced is more than 400 diptera per m² or more than 75 diptera per m³.

* * * * *

UNITED STATES PATENT AND TRADEMARK OFFICE
CERTIFICATE OF CORRECTION

PATENT NO. : 8,716,551 B2 Page 1 of 1
APPLICATION NO. : 12/450026
DATED : May 6, 2014
INVENTOR(S) : Michel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 848 days.

Signed and Sealed this

Twenty-ninth Day of September, 2015

Michelle K. Lee
*Director of the United States Patent and Trademark Office*